United States Patent
Park et al.

(10) Patent No.: US 11,975,095 B2
(45) Date of Patent: May 7, 2024

(54) CALLUS LYSATE COMPRISING HIGH CONTENT OF CALLUS METABOLITE AND PREPARATION METHOD THEREOF

(71) Applicant: BIOSPECTRUM, INC., Yongin-si (KR)

(72) Inventors: Eunyoung Park, Suwon-si (KR); Minho Lee, Osan-si (KR); Eun Sun Jung, Suwon-si (KR); Deok Hoon Park, Seongnam-si (KR)

(73) Assignee: BIOSPECTRUM, INC., Yongin-si (KR)

( * ) Notice: Subject to any disclaimer, the term of this patent is extended or adjusted under 35 U.S.C. 154(b) by 0 days.

(21) Appl. No.: 17/112,591

(22) Filed: Dec. 4, 2020

(65) Prior Publication Data

US 2022/0175655 A1  Jun. 9, 2022

(51) Int. Cl.

| | |
|---|---|
| *A61K 8/9789* | (2017.01) |
| *A61K 8/11* | (2006.01) |
| *A61K 8/31* | (2006.01) |
| *A61K 8/34* | (2006.01) |
| *A61K 8/37* | (2006.01) |
| *A61K 8/41* | (2006.01) |
| *A61K 8/60* | (2006.01) |
| *A61K 8/67* | (2006.01) |
| *A61K 8/73* | (2006.01) |
| *A61K 8/81* | (2006.01) |
| *A61K 8/92* | (2006.01) |
| *A61K 8/9717* | (2017.01) |
| *A61Q 19/00* | (2006.01) |
| *A61Q 19/02* | (2006.01) |
| *A61Q 19/08* | (2006.01) |

(52) U.S. Cl.
CPC ............. *A61K 8/9789* (2017.08); *A61K 8/11* (2013.01); *A61K 8/31* (2013.01); *A61K 8/342* (2013.01); *A61K 8/345* (2013.01); *A61K 8/347* (2013.01); *A61K 8/375* (2013.01); *A61K 8/41* (2013.01); *A61K 8/602* (2013.01); *A61K 8/678* (2013.01); *A61K 8/73* (2013.01); *A61K 8/731* (2013.01); *A61K 8/732* (2013.01); *A61K 8/733* (2013.01); *A61K 8/735* (2013.01); *A61K 8/8182* (2013.01); *A61K 8/922* (2013.01); *A61K 8/9717* (2017.08); *A61Q 19/007* (2013.01); *A61Q 19/02* (2013.01); *A61Q 19/08* (2013.01)

(58) Field of Classification Search
CPC ...... A61K 8/9789; A61K 8/9717; A61K 8/11; A61K 8/31; A61K 8/342; A61K 8/345; A61K 8/347; A61K 8/375; A61K 8/41; A61K 8/602; A61K 8/678; A61K 8/73; A61K 8/731; A61K 8/732; A61K 8/733; A61K 8/735; A61K 8/8182; A61K 8/922; A61Q 19/007; A61Q 19/02; A61Q 19/08
See application file for complete search history.

(56) References Cited

U.S. PATENT DOCUMENTS

| | | | |
|---|---|---|---|
| 2010/0316720 A1* | 12/2010 | Stutz ...................... | A61K 36/05 424/195.17 |
| 2012/0195948 A1* | 8/2012 | Blum .................. | A61K 8/9789 977/799 |
| 2014/0079639 A1* | 3/2014 | McDaniel .......... | G01N 33/5023 424/769 |
| 2020/0179275 A1* | 6/2020 | Rahimi .................. | A61K 9/006 |

FOREIGN PATENT DOCUMENTS

| | | |
|---|---|---|
| KR | 10-2016-0109764 | 9/2016 |
| KR | 10-2020-0004134 | 1/2020 |
| KR | 10-2104225 | 4/2020 |

OTHER PUBLICATIONS

Soysal, Cigdem. "Kinetics and Thermal Activation/Inactivation of Starking Apple Polyphenol Oxidase." Journal of Food Processing and Preservation, 2008, 32: 1034-1046. (Year: 2008).*
Seunghee Ko, "Functional characterization of callus extracts of apple 'Hirosaki' for cosmetic materials", Master of Science Degree Thesis of JEJU National University, Jan. 2013, English Abstract Only.

* cited by examiner

*Primary Examiner* — Doan T Phan
(74) *Attorney, Agent, or Firm* — LEX IP MEISTER, PLLC

(57) ABSTRACT

Disclosed is a callus lysate containing a callus metabolite without a loss of callus metabolite and its preparation method, a capsule containing a callus lysate prepared through encapsulation by coating the callus lysate with a natural polymer material and its preparation method, and composition for external skin application and a cosmetic composition that includes the callus lysate or the capsule containing the callus lysate as an active ingredient, wherein the callus lysate of the present invention contains a large amount of a callus metabolite without a loss of callus metabolite and thus allows penetration or absorption of callus metabolite directly into the skin, thereby providing effects of the callus metabolite to prevent and improve various skin diseases and symptoms.

5 Claims, No Drawings

CALLUS LYSATE COMPRISING HIGH CONTENT OF CALLUS METABOLITE AND PREPARATION METHOD THEREOF

FIELD OF THE INVENTION

The present invention relates to a callus lysate having a high content of callus metabolites, a preparation method for the callus lysate, and a composition including the callus lysate.

BACKGROUND OF THE INVENTION

Callus, in botany, generally refers to an unorganized mass of undifferentiated plant parenchyma cells. The callus is also called plant stem cell because of its ability to differentiate into a whole plant through treatment with plant growth regulators or the like. In recent years, plant tissue culture techniques have developed to produce various plant-derived metabolites through a mass culture of callus cells without damaging plants. The callus culture is therefore of great industrial value.

Callus is a plant-derived cell and thus surrounded by a cell wall made of cellulose, pectin, and lignin that are not degradable in the human body. For this reason, even if the callus itself is applied to human skin, the metabolites contained in the callus are impossible to take in through the human skin, because the human skin has no cellulase to decompose the cell wall of the callus, and the physical force of pressing the callus on the skin with hands for application to the skin is not strong enough to break down the cell wall. That is, the metabolites in the callus are not available for use as a beneficial component directly on the human skin just by applying the callus itself to the skin.

Therefore, various methods have been attempted to use the metabolites contained in the callus as beneficial components in the human body. One of those methods is a method of using extraction, separation, and purification of the beneficial components from a callus with an organic solvent having a high solubility to a specific component. However, the method is problematic in that it has difficulty in extracting beneficial components with high efficiency and uses a large amount of organic solvents not acceptable to human skin in a repeating process of fractionation and concentration to acquire a given content of the beneficial components. Another method involves supercritical extraction or the like that does not use organic solvents. Yet, the supercritical extraction method requires expensive equipment and high energy consumption for the operation of the process, so it is difficult to obtain economic feasibility that can be advantageous with this method.

Moreover, the conventional extraction methods cannot make use of all the nutrients of a plant, but involve highly integrating only some of the beneficial components to lose or waste the other beneficial components than those highly integrated. Eventually, they cannot use the metabolites contained in the callus to the fullest extent, but make a profit not that great for the cost.

All the conventional callus-related patents such as Korean Registered Patent Nos. 10-1791641 and 10-0931768 and Korean Published Patent No. 10-2020-0011239 involve solvent extraction or supercritical extraction of callus and application of beneficial components contained in the callus to the human skin and also have those problems as mentioned above, which still need to be resolved.

Accordingly, the inventors of the present invention have made sustained efforts to develop a method for using metabolites contained in a callus as useful components in the human body and have found it out that performing mechanical homogenization of the callus at a specific pressure not only allows applying the metabolites in the callus to the human body as beneficial components without a loss of callus metabolites, but remarkably enhances penetration and absorption of the metabolites in the callus into the human skin, significantly increasing the various beneficial effects of the metabolites in the callus on the human skin, thereby completing the present invention.

SUMMARY OF THE INVENTION

It is an object of the present invention to provide a method for preparing a callus lysate containing metabolites of a callus without a loss of callus metabolites, the method including a step of performing mechanical homogenization of a callus at a predetermined pressure.

It is another object of the present invention to provide a callus lysate prepared by the method.

It is still another object of the present invention to provide a method for encapsulating the callus lysate to enhance preservation and stability of the callus lysate.

It is further another object of the present invention to provide a capsule containing the encapsulated callus lysate.

It is further another object of the present invention to provide a composition with improved skin penetration and skin absorption of callus metabolites, the composition including the callus lysate or the capsule containing a callus lysate.

It is further another object of the present invention to provide a composition for external skin application for improving skin moisturization, preventing or improving skin wrinkles, whitening skin, enhancing skin elasticity, or improving skin tone, the composition for external skin application including the above composition.

It is further another object of the present invention to provide a cosmetic composition for improving skin moisturization, preventing or improving skin wrinkles, whitening skin, enhancing skin elasticity, or improving skin tone, the cosmetic composition including the above composition.

It is still further another object of the present invention to provide a method for improving skin moisturization, preventing or improving skin wrinkles, whitening skin, enhancing skin elasticity, or improving skin tone, the method including administering the composition for external skin application or the cosmetic composition to an individual biological subject.

In one aspect, the present invention provides a method for preparing a callus lysate containing a callus metabolite without a loss of callus metabolite that includes a step of performing mechanical homogenization of a callus at a predetermined pressure.

The term "callus" as used herein refers to an unorganized mass of undifferentiated plant parenchyma cells, including a callus isolated from plant tissue, a callus obtained by inducing dedifferentiation of a plant section, or a callus grown by the culture of the callus.

The term "plant" as used herein refers to both woody plants and herbaceous plants. Examples of the plant may include fruit trees, e.g., apple tree, pear tree, persimmon tree, grape tree, and ginkgo tree, conifers, e.g., pine, nut pine, and dawn redwood, broad-leaved trees, e.g., forsythia, magnolia, and cherry tree, herbaceous annuals, e.g., cosmos, rose moss, and beans, herbaceous biennials, e.g., barley, wheat, shepherd's purse, and thale cress, and herbaceous perennials, e.g., dandelion, bellflower, and mugwort.

DETAILED DESCRIPTION OF THE INVENTION

In a specific example, a large amount of callus can be produced in a method of sterilizing the branches of a plant, placing them in a callus induction medium, inducing a callus, and then subculturing the induced callus.

The callus induction medium may be a basic medium known in the related art, such as MS, SH, N6, or B5 medium. The callus induction medium, a solid medium, may include agar, gellite, and the like in addition to the basic medium. The medium may further include sugar, inorganic salts, vitamins, amino acids, growth regulators, etc., as necessary. Examples of the growth regulator may include, but not limited to, indole acetic acid (AA), naphthalene acetic acid (NAA), zeatin, 6-benzylaminopurine (BA), and kinetin. The growth regulator may be used alone or in combination with one or more other growth regulators.

The callus induction may be carried out under temperature conditions known in the related art, e.g., 20 to 30° C., for an induction period, e.g., 5 to 10 weeks.

The callus subculture may be performed in a callus culture medium well known in the related art, preferably a liquid medium contained in an air-lift bioreactor. Examples of the liquid medium include an MS medium or an SH medium. The medium may further include sugar, inorganic salts, vitamins, amino acids, growth regulators, etc., in addition to the MS or SH medium, as necessary.

The callus subculture may be carried out under temperature conditions known in the related art, e.g., 20 to 30° C., for a subculture period, e.g., 2 to 6 weeks.

Accordingly, the method for preparing a callus lysate containing a callus metabolite according to the present invention may further include collecting a callus prior to the mechanical homogenization of the callus under high pressure.

The step of collecting a callus includes, as described above, collecting a callus isolated from plant tissue and/or collecting a callus produced by inducing dedifferentiation of a plant section.

In addition, the step of collecting a callus may include collecting a grown callus obtained by callus culture using the callus isolated from plant tissue or the callus produced by induced dedifferentiation of a plant section.

The callus culture may be carried out, as described above, in a callus culture medium well known in the related art, particularly, a liquid medium contained in an air-lift bioreactor. Examples of the liquid medium include an MS medium or an SH medium. The medium may further include sugar, inorganic salts, vitamins, amino acids, growth regulators, etc., in addition to an MS or SH medium, as necessary.

In addition, the callus of the present invention includes somatic embryos resulting from the differentiation of a callus. In this disclosure, the callus includes somatic embryos obtained by differentiation of a callus, unless otherwise stated.

The method for preparing a callus lysate containing a callus metabolite without a loss of callus metabolite according to the present invention may include performing mechanical homogenization of a callus under high pressure.

The term "mechanical homogenization" as used herein refers to disruption and homogenization of a target material with a ball/bead mill, rotor-stator, or blade-type homogenizer according to a mechanical approach.

The mechanical homogenization is conducted under high-pressure conditions, i.e., 200 to 2,000 bar, more preferably 300 to 1,800 bar, and even more preferably 500 to 1,500 bar. When the pressure range is below 200 bar, the efficiency of exposing the metabolites in the callus to the outside of the cell wall is too low to expect the effects of the callus metabolites. When the pressure range is above 2,000 bar, the excessive pressure causes a change in properties and appearance or destruction of the metabolites, especially, beneficial components, in the callus, making it difficult to acquire the effects of the callus metabolites, and renders the callus metabolites susceptible to change in color and odor qualities and hence unsuitable for use in the after-mentioned compositions.

In addition, the mechanical homogenization process is conducted under high-pressure conditions for a cycle time of 15 to 30 minutes, preferably 18 to 22 minutes, more preferably 19 to 21 minutes, and most preferably 20 minutes. Further, the mechanical homogenization process is performed 2 to 5 times, preferably 2 to 4 times, and more preferably 3 times. If the frequency and cycle time of the mechanical homogenization process are below the defined range, the cell wall that prevents the elution and dispersion of the callus metabolites is not sufficiently disrupted, so the callus metabolites can be eluted or dispersed to only a small extent. If the frequency and cycle time of the mechanical homogenization are above the defined range, the cell wall is sufficiently broken apart while the frequency and cycle time are in the defined range, and its further disruption does not occur, which is inefficient.

As such, the mechanical homogenization of callus at high pressure weakens and breaks the binding force of the constituent components (e.g., cellulose, pectin, and lignin or cutin) of the cell wall preventing the elution of the callus metabolites through mechanical shearing force, cavitation, or so. This not only facilitates the elution and dispersion of the callus metabolites but also allows the callus metabolites to exist naturally in the form of a callus lysate together with the remains of the constituent components of the destroyed cell wall. In addition, the mechanical homogenization results in destroying not just a part of the cell wall, but at least 50%, preferably at least 60%, more preferably at least 70%, even more preferably at least 80%, and even more preferably at least 90% of the cell wall, which accelerates the elution and dispersion of the callus metabolites and renders the callus metabolites to naturally exist as a callus lysate together with the remains of the constituent components of the destroyed cell wall.

The term "callus metabolite" as used herein refers to a substance containing components beneficial to human skin that are produced by the organelles of a callus, including, but not limited to, a component for improving skin moisturization, a component for preventing or improving skin wrinkles, a component for whitening skin, a component for enhancing skin elasticity, and a component for improving skin tone.

The term "a loss of callus metabolite" as used herein means that the content of a specific reference substance contained in a callus lysate prepared according to the method of the present invention is 1.3 times, preferably 1.25 times, and more preferably 1.2 times less than the content of the specific reference substance in a callus lysate obtained by a method different from the method of the present invention, such as a method performed in the same manner as the present invention method except for the mechanical homogenization of the callus being performed under the pressure of 100 bar, or in a hot water extract of the callus prepared by another method different from the present invention method. Accordingly, the term "without loss of callus metabolite" as used herein means that the content of a specific reference substance contained in a callus lysate according to the method of the present invention is 1.2 times, preferably 1.25 times, and more preferably 1.3 times greater than the content of the specific reference substance contained in a callus lysate obtained by a method different from the present invention method, such as a method that is all the same as the present invention method except for performing the mechanical homogenization of the callus under the pressure of 100 bar, or in a hot water extract of callus prepared by a method different from the present invention method. Examples of the specific reference substance may include, but not limited to, flavonoids and terpenoids.

The term "callus lysate" as used herein means that callus metabolites and callus (preferably, callus organelles) of which the cell walls are destroyed by the above-described method are present in a dispersed or dissolved state. In the present invention, the callus lysate is characterized by being prepared according to the above-described method and hence also referred to as "callus high-pressure homogenate" for convenience.

On the other hand, the method for preparing a callus lysate containing a callus metabolite according to the present invention may further include, if necessary, removing the callus lysate of cell organelles unbeneficial to human skin, such as nuclei, mitochondria, and vacuole, after performing mechanical homogenization of the callus under high pressure.

The removal of the components unbeneficial to human skin from the callus lysate may be performed by any appropriate method selected depending on the target component to remove, such as filtration, centrifugation, enzyme treatment, or column chromatography.

In another aspect, the present invention provides a callus lysate prepared as described above.

The callus lysate of the present invention is characterized by being prepared through mechanical homogenization of a callus under high pressure. Particularly, the callus lysate of the present invention is a substance in which the bonds of the components constituting the cell wall of the callus are broken through mechanical shearing force and cavitation to shear different parts of the cell wall. This allows the elution of callus metabolites to be easier without a loss of callus metabolites.

The term "loss of callus metabolite(s)" as used herein means that the content of a specific reference substance contained in a callus lysate according to the method of the present invention is 1.3 times, preferably 1.25 times, and more preferably 1.2 times less than the content of the specific reference substance contained in a callus lysate obtained by a method different from the present invention method, such as a method that is all the same as the present invention method except for performing the mechanical homogenization of the callus under the pressure of 100 bar, or in a hot water extract of callus prepared by a method different from the present invention method. Accordingly, the term "without a loss of callus metabolite" as used herein means that the content of a specific reference substance contained in a callus lysate according to the method of the present invention is 1.2 times, preferably 1.25 times, and more preferably 1.3 times greater than the content of the specific reference substance contained in a callus lysate obtained by a method different from the present invention method, such as a method that is all the same as the present invention method except for performing the mechanical homogenization of the callus under the pressure of 100 bar, or in a hot water extract of callus prepared by a method different from the present invention method. Examples of the specific reference substance may include, but not limited to, flavonoids and terpenoids.

More specifically, the conventional callus extract has a problem in that only the beneficial components soluble in a specific solvent are extracted into the callus extract, so there is no way to use the beneficial components insoluble in the specific solvent. In addition, the conventional callus supercritical extraction may involve insufficient destruction of the cell wall, making it difficult to elute the callus metabolites, and require high energy consumption and expensive equipment to break the cell wall in order to facilitate the elution of the callus metabolites. Further, the conventional ultrasonic homogenization of callus is not effective to reduce plant cells to a size small enough to allow the plant cells absorbed into the human skin and, even if the callus lysate can be prepared, its preparation requires a very long processing time and has a limitation in processing the callus in large quantities available for commercial use.

In contrast, the callus lysate prepared according to the present invention has the following advantages over the above-described conventional callus-using techniques.

(1) The callus lysate prepared according to the present invention is obtained by disrupting different parts of the callus cell wall with low energy consumption for a short period of time, allowing the elution of callus metabolites to be easier.

In a specific example, the callus lysate prepared according to the present invention has a significantly higher content of flavonoids and terpenoids than a callus lysate prepared by the conventional method (e.g., hot water extract of callus) under another pressure conditions.

(2) In the callus lysate prepared according to the present invention, callus metabolites are present in a state of being naturally dispersed or dissolved together with the constituent components of the disrupted cell wall due to the disruption of the callus cell wall. This advantageously allows it to use all the components in the calls metabolites beneficial to human skin.

In a specific example, the callus lysate of the present invention is far more effective in improving skin moisturization, preventing or improving skin wrinkles, whitening skin, enhancing skin elasticity, and improving skin tone than a callus lysate obtained by a conventional method (e.g., hot water extract of callus) under another pressure conditions.

(3) In the callus lysate prepared according to the present invention, callus metabolites are present in a dispersed or dissolved state due to the disruption of the callus cell wall, securing high penetration and absorption into the human skin.

In a specific example, the callus lysate of the present invention is 2.04 to 8 times higher in the skin permeability than a callus lysate obtained by a conventional method (e.g., hot water extract of callus) under another pressure conditions.

In further another aspect, the present invention provides a capsule containing a callus lysate that is prepared through encapsulation by coating the above-described callus lysate with a natural polymer material.

The callus lysate contained in the capsule of the present invention is as described above.

In the capsule of the present invention, the natural polymer material is a material derived from plants, minerals, or microorganisms, preferably a thermoplastic material that is solid at room temperature and melts by body temperature, frictional heat, or pressure upon applied to the skin. Examples of the natural polymer material may include, but not limited to, at least one selected from agar, pectin, alginic acid, alginate, carrageenan, curdran, starch, gellan gum, glucomannan, locust gum, guar gum, tara gum, gum Arabic, xanthan gum, hyaluronic acid, karaya gum, tragacanth gum, larch gum, dextran, cellulose, and a mixture thereof.

The encapsulation of the present invention is characterized by the callus lysate being emulsified and dispersed in a liquid-state natural polymer.

The emulsification may be preparing the callus lysate into a solubilized formulation or an emulsion formulation such as water-in-oil (W/O) emulsion, oil-in-water (O/W) emulsion, water-in-oil-in-water (W/O/W) emulsion, or oil-in-water-in-oil (O/W/O) emulsion.

The emulsification may involve using a surfactant or an emulsifier, which may be ionic or nonionic. Examples of the surfactant or emulsifier may include poloxamer or pluronic, polyethylene glycol, polyethylene glycol monostearate, polysorbate, sodium lauryl sulfate, polyethoxylated castor oil, and hydrogenated castor oil. Here, the surfactant or emulsifier may be used in an amount of 5 to 30 parts by weight, preferably 5 to 20 parts by weight, with respect to 100 parts by weight of the callus lysate.

The natural polymer material, as a thermoplastic material, may be liquefied at elevated temperatures of 50° C. or above, preferably 50 to 90° C., more preferably 60 to 90° C., even more preferably 70 to 90° C., and most preferably 80 to 90° C.

In the capsule of the present invention, the weight ratio of the natural polymer material to the callus lysate is 1:0.001 to 1:10, specifically 1:0.005 to 1:10, and more specifically 1:0.05 to 1:10. If the weight ratio is in the above-defined range, the capsule can enhance the preservation and stability of the active ingredient, callus lysate, and provide qualities favorable for better application to the skin when used on the skin, while increasing the preservation of the active ingredient, the callus lysate, in the storage environment.

The capsule of the present invention may have an average particle size of 0.1 to 30 mm, specifically 0.5 to 10 mm, and more specifically 1 to 10 mm. If the average particle size is in the above-defined range, it may improve the preservation and stability of the callus lysate contained in the capsule.

In order to get melt better and more spreadable for better application to the skin, the capsule of the present invention may have a melting point of 30 to 50° C., preferably 35 to 45° C., and more preferably 36° C. or higher, which is for the stability of the capsule, and 45° C. or lower, which is for the compatibility and spreadability of the capsule.

The capsule containing a callus lysate according to the present invention enhances the preservation and stability of the active ingredient, callus lysate, and provides qualities favorable for better application to the skin when used on the skin, while increasing the preservation of the active ingredient, the callus lysate, in the storage environment.

In further another aspect, the present invention provides a method for preparing a capsule containing a callus lysate that includes preparing the above-specified callus lysate and then coating the prepared callus lysate with a natural polymer material to encapsulate the callus lysate.

The callus lysate is as described above, and a description thereof will be omitted below.

The step of preparing the callus lysate, as described above, is defined as performing mechanical homogenization of a callus at a pressure of 200 to 2,000 bar; or performing mechanical homogenization of a callus, and removing component unbeneficial to the human skin from the resultant mechanical homogenate of the callus; or collecting a callus, performing mechanical homogenization of the collected callus, and removing components unbeneficial to the human skin from the resultant mechanical homogenate of the callus. The step of preparing the callus lysate is described above, and reference will be made to the above description.

The step of coating the prepared callus lysate with a natural polymer material to encapsulate the callus lysate is emulsifying the callus lysate and dispersing an emulsion of the callus lysate in a liquid-state natural polymer material to encapsulate the callus lysate.

The emulsification may be preparing the callus lysate into a solubilized formulation or an emulsion formulation such as water-in-oil (W/O) emulsion, oil-in-water (O/W) emulsion, water-in-oil-in-water (W/O/W) emulsion, or oil-in-water-in-oil (O/W/O) emulsion.

The emulsification may involve using a surfactant or an emulsifier, which may be ionic or nonionic. Examples of the surfactant or emulsifier may include poloxamer or pluronic, polyethylene glycol, polyethylene glycol monostearate, polysorbate, sodium lauryl sulfate, polyethoxylated castor oil, and hydrogenated castor oil. Here, the surfactant or emulsifier may be used in an amount of 5 to 30 parts by weight, preferably 5 to 20 parts by weight, with respect to 100 parts by weight of the callus lysate.

The natural polymer material is a material derived from plants, minerals, or microorganisms, preferably a thermoplastic material that is solid at room temperature and melts by body temperature, frictional heat, or pressure upon applied to the skin. Examples of the natural polymer material may include, but are not specifically limited to, at least one selected from agar, pectin, alginic acid, alginate, carrageenan, curdran, starch, gellan gum, glucomannan, locust gum, guar gum, tara gum, gum Arabic, xanthan gum, hyaluronic acid, karaya gum, tragacanth gum, larch gum, dextran, cellulose, and a mixture thereof.

The liquid-state natural polymer material may be prepared by liquefying the natural polymer material of the above-described properties at elevated temperatures of 50° C. or above, preferably 50° C. to 90° C., more preferably 60° C. to 90° C., even more preferably 70° C. to 90° C., and most preferably 80° C. to 90° C.

The weight ratio of the natural polymer material to the callus lysate may be 1:0.001 to 1:10, specifically 1:0.005 to 1:10, and more specifically 1:0.05 to 1:10. If the weight ratio is in the above-defined range, the capsule can enhance the preservation and stability of the active ingredient, callus lysate, and provide qualities favorable for better application to the skin when used on the skin, while increasing the preservation of the active ingredient, the callus lysate, in the storage environment.

In order to enhance the stability of the capsule, the encapsulation step may further include dispersing an emulsion of the callus lysate in liquid-state natural polymer material and then controlling the external temperature to 20° C. or lower, specifically −10° C. to 15° C., and more specifically 0° C. to 10° C. In this regard, the temperature control method may include, but not limited to, controlling the temperature with a device including frozen refrigerants, such as silicone oil, mineral oil, paraffin oil, liquid nitrogen, liquid oxygen, and liquid air, where the device is equipped in the outside of a reactor. In this case, it is possible to prepare a capsule containing a callus lysate that is not only easy to control in the weight ratio of the natural polymer material forming the capsule to the callus lysate contained in the capsule, but also excellent in formability.

The capsule thus prepared may have an average particle size of 0.1 to 30 mm, specifically 0.5 to 10 mm, and more specifically 1 to 10 mm. If the average particle size is in the above-defined range, it may more improve the preservation and stability of the callus lysate contained in the capsule.

In further another aspect, the present invention provides a composition with enhanced skin penetration and skin absorption of callus metabolites, the composition including the callus lysate or the capsule containing a callus lysate.

The callus lysate or the capsule containing a callus lysate used in the composition of the present invention is as described above.

The composition with enhanced skin penetration and skin absorption of callus metabolites according to the present invention may contain, as an active ingredient, the callus lysate or the capsule containing a callus lysate in an amount of 0.01 to 100 wt %, preferably 1 to 90 wt %, and more preferably 5 to 80 wt %, with respect to the total weight of the composition.

In a specific example, the active ingredient, i.e., the callus lysate itself or the callus lysate contained in the capsule, is a substance containing callus metabolites and allowing the elution and dispersion of the callus metabolites to be easier without a loss of callus metabolites, as described above. Therefore, as demonstrated in a dermal equivalent permeability testing, the callus lysate of the present invention is 2.04 to 8 times far more excellent in the permeability into a dermal equivalent than a conventional callus lysate obtained as a hot water extract of callus or the like.

Accordingly, the composition of the present invention allows fast skin penetration of a large amount of the callus lysate containing callus metabolites in an eluted or dispersed state and increases skin absorption of the callus lysate. Thus, the composition can offer beneficial effects due to the action of the eluted and dispersed callus metabolites on the skin, including, but not limited to, improving skin moisturization, skin whitening, skin wrinkles, skin elasticity, and skin tone.

In a specific aspect, the present invention provides a composition for external skin application that includes the callus lysate or the capsule containing a callus lysate.

The callus lysate or the capsule containing a callus lysate according to the present invention are as described above.

The composition for external skin application according to the present invention may include, as an active ingredient, a composition having improved skin penetration and skin absorption of callus metabolites, which composition may be included alone or in combination with an excipient as necessary.

The excipient is not specifically limited as long as it is an excipient available for external use. For example, the excipient may include hydrophilic solvents, including purified water, ethanol, etc.; vegetable oils, including jojoba oil, etc.; animal oils, including squalane, etc.; lubricants, including liquid paraffin, etc.; aliphatic alcohols, including cetyl aryl alcohol, etc.; skin conditioners, including propylene glycol, butylene glycol, glycerin, tocopheryl acetate, polyglyceryl-3 methyl glucose distearate, etc.; surfactants, including triethanolamine, glyceryl stearate, etc.; thickeners, including carboxy vinyl polymers, etc.; emulsifiers; preservatives; and fragrances.

The composition for external skin application according to the present invention may include the callus lysate or the capsule containing a callus lysate in an amount of 0.1 to 80 wt %, preferably 1 to 50 wt %, and more preferably 10 to 50 wt %. If the content of the callus lysate or the capsule containing a callus lysate is less than 0.1 wt %, it results in making the effects of the callus lysate to only a small extent. If the content of the callus lysate or the capsule containing a callus lysate is greater than 80 wt. %, the effects of the callus lysate are very small for the content.

The composition for external application has highly excellent effects due to the action of the callus metabolites contained in the callus lysate, including, but not limited to, improving skin moisturization, preventing or improving skin wrinkles, whitening skin, enhancing skin elasticity, or improving skin tone.

In another specific aspect, the present invention provides a quasi-drug composition comprising the callus lysate or the capsule containing the callus lysate.

The callus lysate or the capsule containing a callus lysate according to the present invention is as described above.

The term "quasi-drug" as used herein means items intended to be used to diagnose, treat, improve, reduce, handle, or prevent diseases in humans and animals but less effective than pharmaceuticals. For example, according to the Pharmacist Act, quasi-drugs exclude items used for pharmaceutical purposes and include products used to treat or prevent diseases in humans and animals, but with mild or no direct action on the human body.

Specifically, the quasi-drugs may include formulations for external skin application and personal hygiene products. More specifically, the quasi-drugs may include, but not limited to, disinfectant cleaners, shower foams, mouthwash, disinfecting wet wipes, detergents, hand soaps, or ointments.

When the composition of the present invention is used as a quasi-drug additive, the callus lysate or the capsule containing a callus lysate may be used alone or in combination with other quasi-drugs or quasi-drug ingredients and applied appropriately according to the conventional methods. The added amount of the active ingredient may be appropriately determined depending on the purpose of use.

The quasi-drug composition of the present invention may include the callus lysate or the capsule containing a callus lysate in an amount of 0.1 to 80 wt. %, specifically 1 to 50 wt. %, and more specifically 10 to 50 wt. %. If the content of the callus lysate or the capsule containing the callus lysate is less than 0.1 wt. %, it results in making the effects of the callus lysate to only a small extent. If the content of the callus lysate or the capsule containing the callus lysate is greater than 80 wt. %, the effects of the callus lysate are very small for the content.

The quasi-drug composition has highly excellent effects due to the action of the callus metabolites contained in the callus lysate, including, but not limited to, improving skin moisturization, preventing or improving skin wrinkles, whitening skin, enhancing skin elasticity, or improving skin tone.

In another specific aspect, the present invention provides a cosmetic composition including the callus lysate or the capsule containing a callus lysate.

The cosmetic composition of the present invention may further include ingredients commonly used in cosmetic compositions in addition to the callus lysate or the capsule containing a callus lysate. For example, the cosmetic composition may include typical adjuvants, such as antioxidants, stabilizers, solubilizers, vitamins, pigments, and fragrances, and vehicles.

The cosmetic composition of the present invention may be prepared into any formulation typical in the related art, including, but not limited to, solution, suspension, emulsion, paste, gel, cream, lotion, powder, soap, surfactant-containing cleansing oil, powder foundation, emulsion foundation, wax foundation, and spray. In further detail, the cosmetic composition may be prepared into a formulation such as nourishing cream, astringent, toner, lotion, essence, nourishing gel, or massage cream.

When the formulation of the cosmetic composition is a paste, cream, or gel, the vehicle component in the composition may be animal oil, vegetable oil, wax, paraffin, starch, tragacanth, cellulose derivatives, polyethylene glycol, silicone, bentonite, silica, talc, zinc oxide, and the like.

When the formulation of the cosmetic composition is a powder or spray, the vehicle component in the composition may be lactose, talc, silica, aluminum hydroxide, calcium silicate, or polyamide powder. Particularly, in the case of a spray formulation, the cosmetic composition may further include a propellant such as chlorofluorohydrocarbon, propane/butane, or dimethyl ether.

When the formulation of the cosmetic composition is a solution or emulsion, the vehicle component in the composition may be a solvent, a solubilizer, or an emulsifier, including, but not limited to, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or aliphatic ester of sorbitan.

When the formulation of the cosmetic composition is a suspension, the vehicle component in the composition may be a liquid-state diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, tragacanth, or the like.

When the formulation of the cosmetic composition is a surfactant-containing cleanser, the vehicle component in the composition may be aliphatic alcohol sulfate, aliphatic alcohol ether sulfate, sulfosuccinic acid monoester, isethionate, imidazolinium derivative, methyl taurate, sarcosinate, aliphatic amide ether sulfate, alkylamidobetaine, aliphatic alcohol, aliphatic glyceride, aliphatic diethanolamide, vegetable oil, lanolin derivative, ethoxylated glycerol aliphatic ester, and so forth.

The cosmetic composition of the present invention may include the callus lysate or the capsule containing a callus lysate in an amount of 0.1 to 80 wt %, specifically 1 to 50 wt %, and more preferably 10 to 50 wt %. If the content of the callus lysate or the capsule containing a callus lysate is less than 0.1 wt. %, the effects of the callus lysate can be made to only a small extent. If the content of the callus lysate or the capsule containing a callus lysate is greater than 80 wt. %, it renders the effects of the callus lysate very small for the content.

The cosmetic composition has highly excellent effects due to the action of the callus metabolites contained in the callus lysate, including, but not limited to, improving skin moisturization, preventing or improving skin wrinkles, whitening skin, enhancing skin elasticity, or improving skin tone.

In another specific aspect, the present invention provides a method for improving skin moisturization, preventing or improving skin wrinkles, whitening skin, enhancing skin elasticity, or improving skin tone, the method comprising a step of administering the composition including a callus lysate or a capsule containing a callus lysate to an individual biological subject.

The term "preventing" as used herein is defined as suppressing the onset of a disease or symptom in an individual biological subject who has never been diagnosed with the disease or symptom but is susceptible to the disease or symptom.

The term "improving" or "treating" as used herein means (a) suppressing or (b) alleviating a disease or symptom in an individual biological subject.

The term "individual biological subject" as used herein refers to mammals including humans capable of achieving the above-mentioned objects by the administration of the composition containing a callus lysate or a capsule containing a callus lysate as an active ingredient according to the present invention, the examples of which mammals including humans may include monkey, cow, horse, pig, sheep, dog, cat, rat, mouse, or chimpanzee.

The term "administration" as used herein refers to introducing a defined substance to an individual biological subject by any appropriate method. The route of administration of the composition according to the present invention is oral or parenteral, preferably parenteral, through any general route as long as the composition can reach the target tissue. In addition, the composition of the present invention can be administered by any device designed to move the active substance to a target subject, such as a cell.

A suitable dosage of the composition of the present invention varies depending on the individual biological subject's condition and body weight, the severity of the disease, the dosage form of the drug, and the time. But it may be appropriately selected by those skilled in the art. The callus lysate or the capsule containing a callus lysate may be administered, as necessary, once to five times a day at a daily dose of 1.0 to 3.0 ml for an adult.

The composition is selected from, but not limited to, a composition for external skin application, a cosmetic composition, or a quasi-drug composition.

The composition comprising the callus lysate or the capsule containing a callus lysate according to the present invention may contain the callus lysate or the capsule containing a callus lysate in an amount of 0.1 to 80 wt. %, specifically 1 to 50 wt. %, and more preferably 10 to 50 wt. %, with respect to the total weight of the composition. If the content of the callus lysate or the capsule containing a callus lysate is less than 0.1 wt. %, it results in making the effects of the callus lysate to only a small extent. If the content of the callus lysate or the capsule containing the callus lysate is greater than 80 wt. %, it renders the effects of the callus lysate very small for the content.

The method for preparing a callus lysate according to the present invention is a preparation method of a callus lysate having a high content of callus metabolites even without using any solvent harmful to the human body, but avoiding a loss of callus metabolites, compared to the conventional callus extract or the like. The callus lysate thus prepared by the method contains callus metabolites, which are eluted from a callus and dispersed in the callus lysate, and thus allows a fast penetration and absorption of the callus metabolites directly into the skin. Further, the capsule containing the callus lysate also allows a fast penetration and absorption of the callus metabolites directly into the skin, enhances the preservation and stability of the active ingredient, callus lysate, and provides qualities favorable for better application to the skin when used on the skin, while increasing the preservation of the active ingredient, callus lysate, in the storage environment. In addition, the composition comprising the callus lysate or the capsule containing a callus lysate contains callus metabolites, which are eluted from a callus and dispersed in the callus lysate, and thus shows excellent performances of improving skin moisturization, preventing or improving skin wrinkles, whitening skin, enhancing skin elasticity, or improving skin tone, due to the action of the callus metabolites. Therefore, the composition can be beneficially used as a preparation for skin application, a quasi-drug for skin, and a cosmetic preparation.

EXAMPLES

Hereinafter, a detailed description will be given to better understand the present invention with reference to examples, which are susceptible to various modifications and variations and not construed to limit the scope of the present invention. The examples of the present invention disclosed herein are provided for those skilled in the art to understand the present invention more completely.

Preparation Example 1

Apple tree branches grew that year (scientific name: *Malus pumila*, variety name: Fuji apple, collected part: part including the cambium in tree branches, growth duration: 1-6 months) were soaked in 35 v/v % hydrogen peroxide for 10 minutes and then 70 v/v % ethanol for 1 minute, and subsequently shaken for 30 minutes in a 2 v/v % sodium hypochlorite solution for sterilization.

The sterilized apple tree branches were washed with sterile water five or more times and cut into small sections of about 1 cm. One section thus obtained was placed in a basal medium containing 30 g/L of sucrose, 4.0 g/L of Gelite, 1 ppm of NAA used as a growth regulator, 4.4 g/L of MS powder, and the remainder purified water and cultured for 8 weeks in an incubator at 25° C. to induce callus formation.

The induced callus was subcultured at intervals of 5 weeks to proliferate and purify. The callus induced as described above was inoculated into an air-lift bioreactor, grown by suspension cell culture for 6 weeks in an incubator at 25° C. under dark conditions, and harvested. In this regard, the culture medium was an MS medium prepared in the same volume of the basal medium by excluding Gelite from the basal medium, and the suspension cell culture was conducted for 6 weeks in an incubator at 25° C. under dark conditions.

Preparation Example 2

The procedures were performed in the same manner as described in Preparation Example 1, excepting that *Lycium chinense* branches grew that year (scientific name: *Lycium chinense*, collected part: part including the cambium in branches, nursery period: 1-6 months) were used instead of the apple tree branches grew that year.

Preparation Example 3

The procedures were performed in the same manner as described in Preparation Example 1, excepting that grape tree branches grew that year (scientific name: *Vitis vinifera* L., variety name: Campbell, collected part: part including the cambium in branches, nursery period: 1-6 months) were used instead of the apple tree branches grew that year.

Example 1

500 ml of the apple callus obtained in Preparation Example 1 was collected and submitted to 3 cycles of homogenization at 200 bar with each cycle time of 20 minutes through a high-pressure homogenizer (product name: Scientz-150, manufacturer: Ningbo Scientz Biotechnology Co., Ltd.). The apple callus high-pressure homogenate thus obtained by high-pressure homogenization was processed at 75° C. for 30 minutes for pasteurization and enzyme inactivation in an additional treatment process and then put into use.

Example 2

The procedures were performed to prepare an apple callus high-pressure homogenate in the same manner as described in Example 1, excepting that the pressure of the high-pressure homogenizer was 500 bar.

Example 3

The procedures were performed to prepare an apple callus high-pressure homogenate in the same manner as described in Example 1, excepting that the pressure of the high-pressure homogenizer was 1,000 bar.

Example 4

The procedures were performed to prepare an apple callus high-pressure homogenate in the same manner as described in Example 1, excepting that the pressure of the high-pressure homogenizer was 2,000 bar.

Example 5

500 ml of the *Lycium chinense* callus culture obtained in Preparation Example 2 was collected and submitted to 3 cycles of homogenization at 200 bar with each cycle time of 20 minutes through a high-pressure homogenizer (product name: Scientz-150, manufacturer: Ningbo Scientz Biotechnology Co., Ltd.). The plant callus homogenate thus obtained by high-pressure homogenization was processed at 75° C. for 30 minutes for pasteurization and enzyme deactivation in an additional treatment process and then put into use.

Example 6

The procedures were performed to prepare a *Lycium chinense* callus high-pressure homogenate in the same manner as described in Example 5, excepting that the pressure of the high-pressure homogenizer was 500 bar.

Example 7

The procedures were performed to prepare a *Lycium chinense* callus high-pressure homogenate in the same manner as described in Example 5, excepting that the pressure of the high-pressure homogenizer was 1,000 bar.

Example 8

The procedures were performed to prepare a *Lycium chinense* callus high-pressure homogenate in the same manner as described in Example 5, excepting that the pressure of the high-pressure homogenizer was 2,000 bar.

Example 9

500 ml of the grape callus culture obtained in Preparation Example 3 was collected and submitted to 3 cycles of homogenization at 200 bar with each cycle time of 20 minutes through a high-pressure homogenizer (product name: Scientz-150, manufacturer: Ningbo Scientz Biotechnology Co., Ltd.). The grape callus homogenate thus obtained by high-pressure homogenization was processed at 75° C. for 30 minutes for pasteurization and enzyme deactivation in an additional treatment process and then put into use.

Example 10

The procedures were performed to prepare a grape callus high-pressure homogenate in the same manner as described in Example 9, excepting that the pressure of the high-pressure homogenizer was 500 bar.

Example 11

The procedures were performed to prepare a grape callus high-pressure homogenate in the same manner as described in Example 9, excepting that the pressure of the high-pressure homogenizer was 1,000 bar.

Example 12

The procedures were performed to prepare a grape callus high-pressure homogenate in the same manner as described in Example 9, excepting that the pressure of the high-pressure homogenizer was 2,000 bar.

Comparative Example 1

500 ml of the apple callus culture obtained in Preparation Example 1 was collected, removed of the culture medium, soaked in 1 L of sterile water, and then submitted to hot water extraction at 80° C. for 60 minutes. The extract solution thus obtained was filtered through a filter paper (Advantes, No. 2) to prepare a hot water extract of callus.

Comparative Example 2

500 ml of the *Lycium chinense* callus culture obtained in Preparation Example 2 was collected, removed of the culture medium, soaked in 1 L of sterile water, and then submitted to hot water extraction at 80° C. for 60 minutes. The extract solution thus obtained was passed through a filter paper (Advantes, No. 2) to prepare a hot water extract of *Lycium chinense* callus.

Comparative Example 3

500 ml of the grape callus culture obtained in Preparation Example 3 was collected, removed of the culture medium, soaked in 1 L of sterile water, and then submitted to hot water extraction at 80° C. for 60 minutes. The extract solution thus obtained was passed through a filter paper (Advantes, No. 2) to prepare a hot water extract of grape callus.

Comparative Example 4

The procedures were performed to prepare a grape callus high-pressure homogenate in the same manner as described in Example 9, excepting that the pressure of the high-pressure homogenizer was 100 bar.

Comparative Example 5

The procedures were performed to prepare a grape callus high-pressure homogenate in the same manner as described in Example 9, excepting that the pressure of the high-pressure homogenizer was 2,100 bar.

Example 13

30 wt % of the grape callus high-pressure homogenate prepared in Example 12, 65 wt % of purified water, and 5 wt % of an emulsifier were mixed, and the resultant mixture was emulsified at 60-70° C. to prepare an oil-in-water (O/W) emulsion.

20 ml of the emulsion was added to 80 ml of a solution prepared by dissolving 2 wt % of agar used as a natural polymer material in 98 wt % of purified water at elevated temperatures of 80-90° C. and dispersed for encapsulation for 2 hours under the same temperature conditions. The capsule thus obtained had an average particle size of about 5 mm.

Example 14

The ingredients given by the composition of the following Table 1 were mixed in a reactor and emulsified at elevated temperature of 70° C. Upon completion of emulsification, the reactor temperature was reduced to 45° C. The capsule containing the grape callus as prepared in Example 13 was mixed and dispersed into a composition, which was then cooled down to 30° C. to prepare a cosmetic formulation of nourishing cream.

Comparative Example 6

The ingredients given by the composition of the following Table 1 were mixed in a reactor and emulsified at elevated temperature of 70° C. Upon completion of emulsification, the reactor temperature was reduced to 45° C. The capsule callus extract prepared in Comparative Example 3 was mixed and dispersed into a composition, which was then cooled down to 30° C. to prepare a cosmetic formulation of nourishing cream.

Comparative Example 7

The ingredients given by the composition of the following Table 1 were mixed in a reactor and emulsified at elevated temperature of 70° C. Upon completion of emulsification, the reactor temperature was reduced to 45° C. The emulsion was dispersed and then cooled down to 30° C. to prepare a cosmetic formulation of nourishing cream.

TABLE 1

| Ingredients (wt %) | Example 14 | Comparative Example 6 | Comparative Example 7 |
|---|---|---|---|
| Grape callus homogenate of Example 12 | 15 | — | — |
| Grape callus extract of Comparative Example 3 | — | 15 | — |
| Jojoba oil | 5 | 5 | 5 |
| Liquid paraffin | 7 | 7 | 7 |
| Cetylaryl alcohol | 2 | 2 | 2 |
| Polyglyceryl-3 methyl glucose distearate | 2 | 2 | 2 |
| Glyceryl stearate | 0.5 | 0.5 | 0.5 |
| Squalane | 3 | 3 | 3 |
| Propylene glycol | 4 | 4 | 4 |
| Glycerin | 5 | 5 | 5 |
| Triethanol amine | 0.3 | 0.3 | 0.3 |

TABLE 1-continued

| Ingredients (wt %) | Example 14 | Comparative Example 6 | Comparative Example 7 |
|---|---|---|---|
| Carboxy vinyl polymer | 0.3 | 0.3 | 0.3 |
| Tocopheryl acetate | 0.2 | 0.2 | 0.2 |
| Preservative, fragrance | — | 0.1 | — |
| Purified water | 65.7 | 55.6 | 70.7 |
| Total | 100 | 100 | 100 |

Experimental Example 1: Evaluation of Skin Penetration Performance

A dermal equivalent (DE) was used to measure the skin penetration effect of the samples of Examples 1 to 12 and Comparative Examples 1 to 5.

The dermal equivalent was prepared by culturing human normal fibroblasts in a medium containing collagen and DMEM (Dulbecco's modification of Eagle's Medium) in a 5% $CO_2$ incubator at 37° C. for 24 hours and then culturing epidermal keratinocyte on the surface of the human normal fibroblasts in K-SFM (Keratinocyte Serum Free Medium) containing EGF (Epidermal Growth Factor) and BPE (Bovine Pituitary Extract) for 7 days to form a multilayered epidermis-dermis structure.

Each sample of Examples 1 to 12 and Comparative Example 1 to 5 was applied to the uppermost layer of the dermal equivalent prepared under the same incubation conditions. After 4 hours of incubation, the amount of the sample penetrating into the dermal equivalent was analyzed by HPLC. The experimental results are presented in Table 2 below. The substances used as a reference for the HPLC analysis's permeability were chlorogenic acid, rutin, resveratrol, etc.

TABLE 2

| Div. | | Permeability for dermal equivalent (ug/ml) |
|---|---|---|
| Example 1 | Apple callus homogenate (200 bar) | 13.2 |
| Example 2 | Apple callus homogenate (500 bar) | 19.4 |
| Example 3 | Apple callus homogenate (1000 bar) | 33.7 |
| Example 4 | Apple callus homogenate (2000 bar) | 38.4 |
| Example 5 | Lycium chinense callus homogenate (200 bar) | 12.7 |
| Example 6 | Lycium chinense callus homogenate (500 bar) | 19.4 |
| Example 7 | Lycium chinense callus homogenate (1000 bar) | 32.5 |
| Example 8 | Lycium chinense callus homogenate (2000 bar) | 37.2 |
| Example 9 | Grape callus homogenate (200 bar) | 10.4 |
| Example 10 | Grape callus homogenate (500 bar) | 19.5 |
| Example 11 | Grape callus homogenate (1000 bar) | 32.8 |
| Example 12 | Grape callus homogenate (2000 bar) | 37.8 |
| Comparative Example 1 | Apple callus extract | 4.8 |
| Comparative Example 2 | Lycium chinense callus extract | 5.3 |
| Comparative Example 3 | Grape callus extract | 5.1 |
| Comparative Example 4 | Grape callus homogenate (100 bar) | 8.4 |
| Comparative Example 5 | Grape callus homogenate (2100 bar) | 40.0 |

As can be seen from Table 2, the samples of Examples 1 to 12 including plant callus homogenates prepared from apple callus, Lycium chinense callus, or grape callus through a high-pressure homogenizer at 200-2,000 bar were 2.04 (10.4/5.1) to 8 (38.4/4.8) times far higher in the permeability for dermal equivalent than those of Comparative Examples 1, 2 and 3 using hot water extracts of the same plant calluses.

In addition, the sample of Comparative Example 4 where the pressure for homogenization was below 200 bar showed a lower skin permeability than those of the examples of the present invention and had a large amount of residues including cell walls remaining undisrupted. The sample of Comparative Example 5 where the pressure for homogenization was above 2,000 bar exhibited sufficiently high permeability, but had a change in properties and appearance such as color and odor qualities, showing that the sample was unsuitable for use in compositions for external application.

Experimental Example 2: Evaluation of Skin Moisturizing Performance

A total of 30 male and female participants in their 20's to 50's were recruited to participate in an evaluation of skin moisturizing performance.

Each participant was instructed to apply 10 g of each sample prepared in Examples 1 to 13 and Comparative Examples 1 to 5 on the surface of an abdominal skin region with an area of 2.5 cm×2.5 cm. After 24 hours, the transepidermal water loss (TEWL) was measured using a TEWA evaporation meter (Tewameter TM 210, Germany). The TEWA evaporation meter was designed to automatically calculate and provide an average value of the measurements acquired for a predetermined measurement time. The transepidermal water loss (TEWL) was measured in a constant temperature and humidity room maintained at 22° C. and 40% relative humidity (RH) with no air movement and no direct sunlight. In addition, the measurements for a total of 30 participants were averaged for each sample of Examples and Comparative Examples. The experimental results are presented in Table 3 below.

TABLE 3

| Div. | | TEWL ($g/m^2/h$) |
|---|---|---|
| Example 1 | Apple callus homogenate (200 bar) | 15.2 |
| Example 2 | Apple callus homogenate (500 bar) | 13.7 |
| Example 3 | Apple callus homogenate (1000 bar) | 11.1 |
| Example 4 | Apple callus homogenate (2000 bar) | 10.4 |
| Example 5 | Lycium chinense callus homogenate (200 bar) | 16.3 |
| Example 6 | Lycium chinense callus homogenate (500 bar) | 14.1 |
| Example 7 | Lycium chinense callus homogenate (1000 bar) | 11.5 |
| Example 8 | Lycium chinense callus homogenate (2000 bar) | 10.1 |
| Example 9 | Grape callus homogenate (200 bar) | 14.3 |
| Example 10 | Grape callus homogenate (500 bar) | 12.1 |
| Example 11 | Grape callus homogenate (1000 bar) | 11.2 |
| Example 12 | Grape callus homogenate (2000 bar) | 10.5 |
| Example 13 | Capsule formulation of Grape callus homogenate (2000 bar) | 9.2 |
| Comparative Example 1 | Apple callus extract | 28.4 |
| Comparative Example 2 | Lycium chinense callus extract | 25.4 |
| Comparative Example 3 | Grape callus extract | 26.7 |
| Comparative Example 4 | Grape callus homogenate (100 bar) | 20.3 |
| Comparative Example 5 | Grape callus homogenate (2100 bar) | 19.7 |

As can be seen from Table 3, the samples of Examples 1 to 12 including plant callus homogenates prepared from apple callus, Lycium chinense callus, or grape callus through a high-pressure homogenizer at 200-2,000 bar were far more excellent in skin moisturizing performance than those of Comparative Examples 1, 2 and 3 using hot water extracts of the same plant calluses and Comparative Examples 4 and 5 where the pressure for homogenization was out of the defined range of the present invention.

In particular, the sample of Example 13, a capsule formulation containing a grape callus homogenate coated with agar, was more improved in TEWL due to the combined action as the outer skin of the capsule was also applied to the skin during application of the sample.

Experimental Example 3: Evaluation of Wrinkle Preventing Performance

Antibodies were used to measure the activity of collagenase, an enzyme for breaking down collagen.

Human normal fibroblasts (Pacific Co., Ltd.) were inoculated into a 6-well microplate containing a DMEM medium at a rate of $2\times10^5$ cells/well and cultured in a 5% $CO_2$ incubator at 37° C. for 24 hours. After 24 hours of incubation, the culture medium was removed from each well. The samples were treated by concentration and cultured for another 24 hours. After 24 hours of incubation, the cell culture medium was collected to prepare a test sample.

10 ng/ml of a tumor necrosis factor alpha (TNF-alpha, Sigma, USA), known as a substance inducing collagenase activity, was added to the 6-well microplate in which the human normal fibroblasts were cultured. Using a type 1 collagenase assay kit (Amersham Biosciences, RPN2629), absorbance at 450 nm was determined with an ELISA reader (Bio-Tek ELx808™ Series Ultra Microplate Reader, UK). The control was distilled water. The absorbance measurements were used to calculate the collagenase inhibition rate according to Equation 1 below. The results are presented in Table 4 below.

Collagenase Inhibition Rate (%)=100−{[($A1$−$B1$)−($C1$−$D1$)]/($A1$−$B1$)}×100     [Equation 1]

A1: Absorbance of the control
B1: Blank absorbance of the control
C1: Absorbance of the experimental group
D1: Blank absorbance of the experimental group

TABLE 4

| Div. | | Collagenase inhibition rate (%) |
|---|---|---|
| Example 1 | Apple callus homogenate (200 bar) | 30.2 |
| Example 2 | Apple callus homogenate (500 bar) | 32.7 |
| Example 3 | Apple callus homogenate (1000 bar) | 45.2 |
| Example 4 | Apple callus homogenate (2000 bar) | 47.7 |
| Example 5 | Lycium chinense callus homogenate (200 bar) | 33.5 |
| Example 6 | Lycium chinense callus homogenate (500 bar) | 37.4 |
| Example 7 | Lycium chinense callus homogenate (1000 bar) | 44.2 |
| Example 8 | Lycium chinense callus homogenate (2000 bar) | 47.8 |
| Example 9 | Grape callus homogenate (200 bar) | 33.4 |
| Example 10 | Grape callus homogenate (500 bar) | 39.6 |
| Example 11 | Grape callus homogenate (1000 bar) | 40.6 |
| Example 12 | Grape callus homogenate (2000 bar) | 43.8 |
| Example 13 | Capsule formulation of Grape callus homogenate (2000 bar) | 51.4 |
| Comparative Example 1 | Apple callus extract | 14.8 |
| Comparative Example 2 | Lycium chinense callus extract | 15.4 |
| Comparative Example 3 | Grape callus extract | 14.5 |
| Comparative Example 4 | Grape callus homogenate (100 bar) | 21.8 |
| Comparative Example 5 | Grape callus homogenate (2100 bar) | 29.4 |

As can be seen from Table 4, the samples of Examples 1 to 12 including plant callus homogenates prepared from apple callus, *Lycium chinense* callus, or grape callus through a high-pressure homogenizer at 200-2,000 bar were far more excellent in wrinkle-preventing performance than those of Comparative Examples 1, 2 and 3 using hot water extracts of the same plant calluses and Comparative Examples 4 and 5 where the pressure for homogenization was out of the defined range of the present invention.

In particular, the sample of Example 13, a capsule formulation containing a grape callus homogenate coated with agar, was more improved in collagenase inhibition performance due to the combined action as the outer skin of the capsule was also applied to the skin during application of the sample.

Experimental Example 4: Evaluation of Tyrosinase Inhibition Performance

In this experiment, murine melanoma cells (B-16 F1, Korea Cell Line Bank) were inoculated into a 6-well plate with a DMEM medium containing 10% fetal bovine serum (FBS) at a rate of $1\times10^5$ cells/well and cultured under conditions of 5% $CO_2$ and 37° C. until about 80% or more of the cells were immobilized on the bottom of the wells. Subsequently, the sample was removed of the medium, transferred to another culture medium diluted to an appropriate concentration, and then cultured under conditions of 5% $CO_2$ and 37° C. for 3 days. The cells removed of the medium were washed with phosphate-buffered saline (PBS), treated with trypsin and collected. The cells thus collected were counted using a hematocytometer (Tiefe Depth Profondeur 0.100 mm, Paul Marienfeld GmbH & Co. KG, Germany), centrifuged at 5,000 to 10,000 rpm for 10 minutes, and then removed of the supernatant to obtain a pellet. The cell pellet was pulverized using a lysis buffer and centrifuged at 12,000 rpm for 10 minutes to obtain the supernatant.

The supernatant thus obtained was measured regarding the absorbance at 492 nm with a microplate reader (Bio-Tek ELx8081U, USA) to determine the tyrosinase activity per constant number of cells. The absorbance was used to calculate the tyrosinase inhibition rate according to Equation 2 below. The experimental results are presented in Table 5 below.

The blank of the experimental group was reactants excluding the tyrosinase solution, that is, reactants consisting of tyrosine, a callus homogenate, a callus extract, and a sodium phosphate buffer solution. The blank of the control group was prepared by replacing the callus homogenate and the callus extract with methanol in the blank of the experimental group.

Tyrosinase Inhibition Rate (%)=100−{[($A2$−$B2$)−($C2$−$D2$)]/($A2$−$B2$)}×100     [Equation 2]

A2: Absorbance of the control
B2: Blank absorbance of the control
C2: Absorbance of the experimental group
D2: Blank absorbance of the experimental group

TABLE 5

| Div. | | Tyrosinase inhibition rate (%) |
|---|---|---|
| Example 1 | Apple callus homogenate (200 bar) | 24.4 |
| Example 2 | Apple callus homogenate (500 bar) | 27.1 |
| Example 3 | Apple callus homogenate (1000 bar) | 30.4 |
| Example 4 | Apple callus homogenate (2000 bar) | 33.5 |
| Example 5 | Lycium chinense callus homogenate (200 bar) | 26.7 |
| Example 6 | Lycium chinense callus homogenate (500 bar) | 27.4 |
| Example 7 | Lycium chinense callus homogenate (1000 bar) | 28.6 |
| Example 8 | Lycium chinense callus homogenate (2000 bar) | 32.4 |
| Example 9 | Grape callus homogenate (200 bar) | 25.4 |
| Example 10 | Grape callus homogenate (500 bar) | 29.7 |
| Example 11 | Grape callus homogenate (1000 bar) | 30.1 |
| Example 12 | Grape callus homogenate (2000 bar) | 33.4 |
| Example 13 | Capsule formulation of Grape callus homogenate (2000 bar) | 31.7 |
| Comparative Example 1 | Apple callus extract | 12.6 |
| Comparative Example 2 | Lycium chinense callus extract | 9.7 |
| Comparative Example 3 | Grape callus extract | 12.1 |
| Comparative Example 4 | Grape callus homogenate (100 bar) | 22.3 |
| Comparative Example 5 | Grape callus homogenate (2100 bar) | 25.9 |

As can be seen from Table 5, the samples of Examples 1 to 12 including plant callus homogenates prepared from apple callus, *Lycium chinense* callus, or grape callus through a high-pressure homogenizer at 200-2,000 bar were far more excellent in tyrosinase inhibition performance than those of Comparative Examples 1, 2 and 3 using hot water extracts of the same plant calluses and Comparative Example 4 where the pressure for homogenization was less than 200 bar. In addition, the sample of Comparative Example 5 where the pressure for homogenization was above 2,000 bar had a sufficiently high tyrosinase inhibition performance, but a change in properties and appearance such as color and odor qualities, which showed that the sample was unsuitable for use in formulations for external application or cosmetic compositions.

Further, the sample of Example 13, a capsule formulation containing a grape callus homogenate coated with agar, was also excellent in tyrosinase inhibition performance.

Experimental Example 5: Evaluation of Skin Whitening Performance 100 healthy male and female adult participants with melisma, freckles, or hyperpigmentation were instructed to use the nourishing cream formulations prepared in Example 14 and Comparative Examples 6 and 7 and then measure the variation of skin color brightness (ΔL) with a chromameter (Minolta CR300).

In this experiment, the 100 healthy male and female adult participants with melisma, freckles, or hyperpigmentation were randomly divided into three groups (A, B, C) of 20 people. The participant groups A, B, and C were instructed to apply the experimental group 1, the control group, and the comparative group 1, respectively, on the skin twice daily for 12 weeks and measure the variation of skin brightness. The experimental results are presented in Table 6 below.

TABLE 6

| Participant | Example 14 (Group A) | Comparative Example 6 (Group B) | Comparative Example 7 (Group C) |
|---|---|---|---|
| 1 | 6.2 | 5.7 | 4.4 |
| 2 | 5.4 | 4.9 | 3.4 |
| 3 | 5.6 | 4.8 | 3.0 |
| 4 | 6.6 | 4.5 | 2.4 |
| 5 | 5.7 | 4.1 | 3.6 |
| 6 | 6.6 | 5.7 | 2.4 |
| 7 | 6.3 | 5.9 | 4.1 |
| 8 | 5.1 | 5.2 | 3.3 |
| 9 | 6.8 | 4.7 | 3.4 |
| 10 | 6.1 | 4.2 | 3.8 |
| 11 | 4.9 | 3.8 | 2.6 |
| 12 | 6.2 | 5.4 | 4.5 |
| 13 | 6.3 | 6.2 | 4.2 |
| 14 | 5.6 | 4.1 | 3.4 |
| 15 | 5.8 | 5.0 | 3.7 |
| 16 | 6.3 | 5.3 | 2.2 |
| 17 | 6.7 | 5.4 | 2.5 |
| 18 | 6.9 | 5.2 | 3.5 |
| 19 | 6.5 | 4.9 | 2.9 |
| 20 | 6.1 | 5.1 | 2.7 |
| Average | 6.1 | 5.0 | 3.3 |

As can be seen from Table 6, the nourishing cream formulation of Example 14 including a plant callus homogenate prepared from grape callus through a high-pressure homogenizer at 200-2,000 bar was far more excellent in skin whitening performance than the control using a vehicle (Comparative Example 7) alone. In particular, it had even significantly higher skin whitening performance than the nourishing cream of Comparative Example 6 using a hot water extract of grape callus.

Experimental Example 6: Evaluation of Anti-Oxidation Performance

The antioxidant activity was evaluated by measuring the ability of scavenging a free radical, DPPH (1,1-diphenyl-2-picrylhydrazyl). DPPH, a radical with a color, was used to directly determine the radical scavenging ability of the sample.

50 μl of each sample of Examples 1 to 13 and Comparative Examples 1 to 5 was mixed with 1 ml of a 100 μM DPPH solution. The resultant mixture was subjected to reaction and incubation at 20° C. (room temperature) at 30 minutes. Then, the amount of the remaining DPPH was determined through the absorbance measurement at 517 nm.

Upon completion of the reaction, the free radical scavenging activity (%) of the sample was calculated according to Equation 3 below. The experimental results are presented in Table 7 below. In this regard, the positive control was 400 μg/ml of ascorbic acid, and the blank was purified water.

Radical Scavenging Ability (%)={1−(absorbance of sample-added group/absorbance of sample-free group)×100}  [Equation 3]

TABLE 7

| Div. | | Free radical scavenging ability (%) |
|---|---|---|
| Example 1 | Apple callus homogenate (200 bar) | 80.2 |
| Example 2 | Apple callus homogenate (500 bar) | 83.6 |
| Example 3 | Apple callus homogenate (1000 bar) | 88.5 |
| Example 4 | Apple callus homogenate (2000 bar) | 90.3 |
| Example 5 | Lycium chinense callus homogenate (200 bar) | 77.2 |
| Example 6 | Lycium chinense callus homogenate (500 bar) | 80.9 |

TABLE 7-continued

| Div. | | Free radical scavenging ability (%) |
|---|---|---|
| Example 7 | Lycium chinense callus homogenate (1000 bar) | 84.3 |
| Example 8 | Lycium chinense callus homogenate (2000 bar) | 89.6 |
| Example 9 | Grape callus homogenate (200 bar) | 82.6 |
| Example 10 | Grape callus homogenate (500 bar) | 85.3 |
| Example 11 | Grape callus homogenate (1000 bar) | 87.3 |
| Example 12 | Grape callus homogenate (2000 bar) | 90.1 |
| Example 13 | Capsule formulation of Grape callus homogenate (2000 bar) | 88.8 |
| Comparative Example 1 | Apple callus extract | 50.4 |
| Comparative Example 2 | Lycium chinense callus extract | 38.1 |
| Comparative Example 3 | Grape callus extract | 40.4 |
| Comparative Example 4 | Grape callus homogenate (100 bar) | 37.5 |
| Comparative Example 5 | Grape callus homogenate (2100 bar) | 61.2 |
| Control | Ascorbic acid (400 μg/ml) | 80.7 |
| Blank | Distilled water | 0 |

As can be seen from Table 7, the samples of Examples 1 to 12 including plant callus homogenates prepared from apple callus, *Lycium chinense* callus, or grape callus through a high-pressure homogenizer at 200-2,000 bar and Example 13 prepared as a capsule formulation were far more excellent in anti-oxidation performance than those of Comparative Examples 1, 2 and 3 using hot water extracts of the same plant calluses and Comparative Examples 4 and 5 prepared under pressure out of the defined range of the present invention.

In particular, all the samples of Examples 1 to 13 had far higher radical-scavenging performance even than the positive control, ascorbic acid.

Experimental Example 7: Evaluation of Flavonoid Content 10 ml of each sample of Examples 1 to 13 and Comparative Examples 1 to 5 was filtered through a 0.2 μm syringe filter to prepare a test sample. The total polyphenol content was determined using the Folin-Denis method (Gutfinger R. 1981). 1 mg of each sample was dissolved in 1 ml of distilled water. A ten-fold dilution was made to prepare a diluted solution. 0.2 ml of a Folin-Ciocalteu's phenol reagent was added to 2 ml of the diluted solution, which was then kept at room temperature for 3 minutes. 2 ml of 2M $Na_2CO_3$ was added to the diluted solution to activate a reaction, which lasted for one hour. The resultant supernatant was submitted to a microplate reader for measurement at 725 nm. The content was determined from a standard curve made using the gallic acid standard. The experimental results are presented in Table 8 below.

Experimental Example 8: Evaluation of Terpenoid Content 10 ml of each sample of Examples 1 to 13 and Comparative Examples 1 to 5 was filtered through a 0.2 μm syringe filter to prepare a test sample. Each sample was freeze-dried at −20° C. for 48 hours and then submitted to extraction with petroleum ether (60-80° C.). The extract thus obtained was filtered and concentrated. Then the fraction of the concentrate was analyzed by thin layer chromatography (TLC) on a silica gel C using a benzene-ethyl acetate (99:1) solvent. The sample was analyzed using a glass column by gas-liquid chromatography (Shimadzu GC07A, Kyoto, Japan). Quantification was conducted through a standard curve using the artemisinin standard, and the total terpenoid content was determined by HPLC using a methanol-water (80:20) eluent (0.8 ml/min). The measurement results are presented in Table 8 below.

TABLE 8

| | Flavonoid content (mg/l) | Terpenoid content (mg/l) |
|---|---|---|
| Example 1 | 178.55 | 42.15 |
| Example 2 | 223.44 | 45.48 |
| Example 3 | 267.89 | 52.22 |
| Example 4 | 303.21 | 56.31 |
| Example 5 | 163.63 | 38.66 |
| Example 6 | 186.59 | 42.11 |
| Example 7 | 200.06 | 57.67 |
| Example 8 | 254.64 | 73.32 |
| Example 9 | 201.66 | 33.54 |
| Example 10 | 264.38 | 54.22 |
| Example 11 | 297.69 | 66.45 |
| Example 12 | 321.28 | 78.83 |
| Example 13 | 110.06 | 31.22 |
| Comparative Example 1 | 83.32 | 10.23 |
| Comparative Example 2 | 61.55 | 11.25 |
| Comparative Example 3 | 88.54 | 12.82 |
| Comparative Example 4 | 91.32 | 22.33 |
| Comparative Example 5 | 93.27 | 27.13 |

As shown in Table 8, all the samples of the present invention according to Examples 1 to 13 had a far higher content of components beneficial to the skin, such as flavonoids and terpenoids than those of Comparative Examples 1 5.

Experimental Example 9: Evaluation of Formulation Stability

The samples of Examples 12 and 13 and Comparative Example 3 were evaluated in regards to the stability to light as follows. First of all, 4 aliquots of each sample, with a volume of 30 ml per aliquot, were placed in a light-proof container and a light-permeable container, stored in a thermostat maintained at an illuminance of 1000±200 lux and a temperature of 25±2° C. (room temperature) and then submitted to fast liquid chromatography at intervals of 2 weeks. For a resveratrol analysis by fast liquid chromatography, 0.1 g of each sample was dissolved in 10 ml of 100% pure methanol and submitted to three cycles of pulverization with each cycle time of 10 seconds and then extraction for 12 hours. The extract thus obtained was centrifuged and filtered through a 0.2 μm nylon filter for organic solvent to prepare a test sample solution.

Each 10 μl of the test sample solution and the standard solution was used to determine the peak areas for resveratrol ($C_{14}H_{12}NO_3$), AT (Test area: the area of peaks for the test sample) and AS (Standard area: the area of peaks for the standard sample), according to the liquid chromatography method under the following operational conditions.

Amount of resveratrol ($C_{14}H_{12}NO_3$)(mg)=amount of resveratrol standard product (mg)×AT/AS    [Equation 4]

[Operating Conditions]

Detector: Ultraviolet spectrophotometer

Column: A column having about 5 μm of octadecylsilylated silica gel for liquid chromatograph packed in a stainless steel tube with an inner diameter of 4.6 mm and a length of 15 cm, or an equivalent Column temperature: room temperature
Mobile phase: 0.1% TFA water:acetonitrile=70:30
Flow rate: 1.0 mL/min

TABLE 9

| Light | Time (week) | Amount of remaining resveratrol (%) | | |
|---|---|---|---|---|
| | | Comparative Example 3 | Example 12 | Example 13 |
| Light blocked/light exposure | 0 | 100 | 100 | 100 |
| Light blocked | 2 | 84 | 91 | 100 |
| Light blocked | 4 | 69 | 85 | 98 |
| Light exposure | 2 | 55 | 77 | 93 |
| Light exposure | 4 | 22 | 55 | 76 |

As can be seen from Table 9, it was observed that the grape callus homogenate of Example 12 maintained a higher residual amount of resveratrol than the hot water extract of grape callus of Comparative Example 3. In addition, the stability of resveratrol was noticeably improved in a capsule formulation having the plant callus homogenate coated with agar as in Example 13.

Simple variations or modifications of the present invention can be made by those skilled in the art with ease, and such variations or modifications are all construed to be included in the scope of the present invention.

The invention claimed is:

1. A method for preparing a callus lysate containing a callus metabolite without a loss of callus metabolite, the method comprising
    performing mechanical homogenization of a callus at a pressure of 200 to 1,800 bar,
    pasteurizing the callus homogenate obtained by the homogenization, and
    deactivating enzymes in the callus homogenate at 75° C. to obtain the callus lysate,
    wherein the mechanical homogenization process is performed 2 to 4 times, and for 18 to 22 minutes per time.

2. The method according to claim 1, further comprising at least one of the following steps before the mechanical homogenization step:
    (a) isolating a callus from plant tissue and collecting the isolated callus;
    (b) inducing dedifferentiation of a plant section to produce a callus and collecting the produced callus; or
    (c) culturing the collected callus of step (a) or (b) to grow the callus and collecting the callus.

3. The method according to claim 1, wherein the loss of callus metabolite is having the content of a specific reference substance contained in the callus lysate 1.3 times less than the content of the specific reference substance in a callus lysate prepared by a hot water extract method.

4. The method according to claim 1, wherein the method has at least one effect selected from the group consisting of improving skin moisturization, preventing or improving skin wrinkles, enhancing skin elasticity, whitening skin, and improving skin tone.

5. A method for preparing a capsule containing a callus lysate, the method comprising
    performing mechanical homogenization of a callus at a pressure of 200 to 1,800 bar, wherein the mechanical homogenization process is performed 2 to 4 times, and for 18 to 22 minutes per time;
    pasteurizing the callus homogenate obtained by the homogenization;
    deactivating enzymes in the callus homogenate at 75° C. to obtain the callus lysate; and
    coating the callus lysate with a natural polymer material to encapsulate the callus lysate at a weight ratio of the natural polymer material to the callus lysate is 1:0.001 to 1:10,
    wherein the natural polymer material is at least one selected from the group consisting of agar, pectin, alginic acid, alginate, carrageenan, curdran, starch, gellan gum, glucomannan, locust gum, guar gum, tara gum, gum Arabic, xanthan gum, hyaluronic acid, karaya gum, tragacanth gum, larch gum, dextran, cellulose, and a mixture thereof.

* * * * *